(12) United States Patent
Thalacker et al.

(10) Patent No.: US 12,070,514 B2
(45) Date of Patent: Aug. 27, 2024

(54) ONE-PART DENTAL ADHESIVE COMPOSITION FOR FIXING DENTAL COMPOSITE MATERIALS

(71) Applicant: Solventum Intellectual Properties Company, Maplewood, MN (US)

(72) Inventors: Christoph H. Thalacker, Weilheim (DE); Karsten Dede, Landsberg (DE); Henry Loll, Gilching (DE); Bernd Anich, Andechs (DE); Adrian S. Eckert, Herrsching (DE); Kai U. Claussen, Munich (DE); Manfred Ludsteck, Geretsried (DE)

(73) Assignee: Solventum Intellectual Properties Company, Maplewood, MN (US)

( * ) Notice: Subject to any disclaimer, the term of this patent is extended or adjusted under 35 U.S.C. 154(b) by 479 days.

(21) Appl. No.: 17/052,273

(22) PCT Filed: Apr. 29, 2019

(86) PCT No.: PCT/IB2019/053497
§ 371 (c)(1),
(2) Date: Nov. 2, 2020

(87) PCT Pub. No.: WO2019/211724
PCT Pub. Date: Nov. 7, 2019

(65) Prior Publication Data
US 2021/0085570 A1 Mar. 25, 2021

(30) Foreign Application Priority Data
May 2, 2018 (EP) .................................... 18170337

(51) Int. Cl.
| | |
|---|---|
| A61K 6/30 | (2020.01) |
| A61K 6/61 | (2020.01) |
| A61K 6/62 | (2020.01) |
| A61K 6/824 | (2020.01) |
| A61K 6/887 | (2020.01) |
| C08L 33/02 | (2006.01) |
| C08L 35/00 | (2006.01) |

(52) U.S. Cl.
CPC ............... *A61K 6/30* (2020.01); *A61K 6/61* (2020.01); *A61K 6/62* (2020.01); *A61K 6/824* (2020.01); *A61K 6/887* (2020.01); *C08L 33/02* (2013.01); *C08L 35/00* (2013.01)

(58) Field of Classification Search
CPC ....................................................... A61K 6/30
See application file for complete search history.

(56) References Cited

U.S. PATENT DOCUMENTS

| | | |
|---|---|---|
| 3,541,068 A | 11/1970 | Taylor |
| 4,259,075 A | 3/1981 | Yamauchi |
| 4,499,251 A | 2/1985 | Omura |
| 4,537,940 A | 8/1985 | Omura |
| 4,539,382 A | 9/1985 | Omura |
| 4,642,126 A | 2/1987 | Zador |
| 4,652,274 A | 3/1987 | Boettcher |
| 4,695,251 A | 9/1987 | Randklev |
| 4,795,823 A | 1/1989 | Schmitt |
| 4,872,936 A | 10/1989 | Engelbrecht |
| 5,130,347 A | 7/1992 | Mitra |
| 5,530,038 A | 6/1996 | Yamamoto |
| 5,847,025 A | 12/1998 | Moszner |
| 5,918,772 A | 7/1999 | Keller |
| 5,944,419 A | 8/1999 | Streiff |
| 5,996,796 A | 12/1999 | Kvitrud |
| 6,105,761 A | 8/2000 | Peuker |
| 6,288,138 B1 | 9/2001 | Yamamoto |
| 6,387,981 B1 | 5/2002 | Zhang |
| 6,444,725 B1 | 9/2002 | Trom |
| 6,450,717 B1 | 9/2002 | Salz |
| 6,458,868 B1 | 10/2002 | Okada |
| 6,552,140 B1 | 4/2003 | Kneafsey |
| 6,572,693 B1 | 6/2003 | Wu |
| 6,730,156 B1 | 5/2004 | Windisch |
| 6,899,948 B2 | 5/2005 | Zhang |
| 7,968,617 B2 | 6/2011 | Thalacker |

(Continued)

FOREIGN PATENT DOCUMENTS

| | | |
|---|---|---|
| DE | 102010003883 | 10/2011 |
| EP | 0712622 | 5/1996 |

(Continued)

OTHER PUBLICATIONS

Database CAPLUS [Online] Chemical Abstracts Service, Columbus, Ohio, US; Dec. 11, 2014, Fukutome, "Dental repair kit including primer composition and filling material", XP002786213, Database accession No. 2014:2054014 Abstract, 3 pages.

Sanares, "Adverse surface interactions between one-bottle light-cured adhesives and chemical-cured composites", Dental. Materials, Nov. 2001, vol. 17, No. 6, pp. 542-556.

Suh, "Factors Contributing to the Incompatibility Between Simplified-step Adhesives and Chemically-cured or Dual-cured Composites. Part III. Effect of Acidic Resin Monomers", The Journal of Adhesive Dentistry, 2003 vol. 5, No. 4, 267-282.

(Continued)

*Primary Examiner* — Michael F Pepitone
(74) *Attorney, Agent, or Firm* — Ashley M. Dreis

(57) ABSTRACT

The invention relates to a one-part dental adhesive composition comprising polymerizable component(s) with an acidic moiety as Component A, photo-initiator(s) as Component B1, transition metal ion component(s) as Component C, solvent(s) other than water as Component D1, a stabilizer as Component E, the stabilizer comprising a free radical moiety or being selected from anaerobic stabilizers, for use in a process of fixing a composite material to the surface of hard dental tissue, the composite material comprising a redox initiator system with an oxidizing agent and a reducing agent.

18 Claims, No Drawings

(56) References Cited

U.S. PATENT DOCUMENTS

| | | | |
|---|---|---|---|
| 8,501,834 B2 | 8/2013 | Maletz | |
| 9,056,043 B2 | 6/2015 | Joly | |
| 11,357,708 B2* | 6/2022 | Moszner | A61K 6/887 |
| 2003/0050359 A1 | 3/2003 | Kimura | |
| 2003/0166740 A1 | 9/2003 | Mitra | |
| 2004/0206932 A1 | 10/2004 | Abuelyaman | |
| 2005/0203199 A1 | 9/2005 | Moszner | |
| 2005/0252413 A1 | 11/2005 | Kangas | |
| 2005/0252414 A1 | 11/2005 | Craig | |
| 2005/0256223 A1 | 11/2005 | Kolb | |
| 2006/0187752 A1 | 8/2006 | Keller | |
| 2007/0090079 A1 | 4/2007 | Keller | |
| 2010/0216096 A1 | 8/2010 | Suzuki | |
| 2010/0311864 A1 | 12/2010 | Arita | |
| 2010/0317762 A1* | 12/2010 | Matsushige | A61K 6/71 523/118 |
| 2011/0112208 A1* | 5/2011 | Sang | A61K 6/30 522/28 |
| 2012/0115108 A1* | 5/2012 | Blomker | C08F 230/02 523/105 |
| 2013/0018123 A1 | 1/2013 | Liu | |
| 2014/0329205 A1* | 11/2014 | Hecht | A61C 19/003 522/28 |
| 2016/0051450 A1 | 2/2016 | Kashiki | |

FOREIGN PATENT DOCUMENTS

| | | | |
|---|---|---|---|
| EP | 1051961 | 11/2000 | |
| EP | 2258336 | 12/2010 | |
| EP | 2412361 | 2/2012 | |
| JP | 2014-231493 | 12/2014 | |
| WO | WO 2003-063804 | 8/2003 | |
| WO | WO 2011-056814 | 5/2011 | |
| WO | WO 2013-082337 | 6/2013 | |
| WO | WO 2015-051217 | 4/2015 | |
| WO | WO-2016110571 A1 * | 7/2016 | A61K 6/005 |
| WO | WO 2019-010154 | 1/2019 | |
| WO | WO 2019-092580 | 5/2019 | |

OTHER PUBLICATIONS

Tay, "Factors Contributing to the Incompatibility Between Simplified-step Adhesives and Chemically-cured or Dual-cured Composites. Part I. Single-step Self-etching Adhesive", The Journal of Adhesive Dentistry, 2003, vol. 5, No. 1, pp. 27-40.

Tay, "Factors Contributing to the Incompatibility Between Simplified-step Adhesives and Self-cured or Dual-cured Composites. Part II. Single-bottle, Total-etch Adhesive", The Journal of Adhesive Dentistry, 2003, vol. 5, No. 2, pp. 91-105.

Technical Product Profile, "3M Scotchbond™—Multi-Purpose Plus—Dental Adhesive System", 1994, 40 pages.

1507 Extended EP Search Report for EP18170337.2, Date Nov. 11, 2018, 33pgs.

International Search Report for PCT International Application No. PCT/IB2019/053497, mailed on Jan. 17, 2020, 5 pages.

* cited by examiner

ONE-PART DENTAL ADHESIVE COMPOSITION FOR FIXING DENTAL COMPOSITE MATERIALS

CROSS REFERENCE TO RELATED APPLICATIONS

This application is a national stage filing under 35 U.S.C. 371 of PCT/IB2019/053497, filed 29 Apr. 2019, which claims the benefit of European Patent Application No. 18170337.2, filed 2 May 2018, the disclosures of which are incorporated by reference in their entireties herein.

FIELD OF THE INVENTION

The invention relates to an acidic dental adhesive composition comprising a transition metal component for use in a process of adhering a self-cure or dual-cure dental composite material comprising a redox initiator system containing an oxidizing agent and a reducing agent to the surface of hard dental tissue.

The invention also relates to a kit of parts comprising such a dental adhesive composition and a dental composite material.

BACKGROUND

For establishing a bond to hard dental tissue, modern dental adhesives typically contain acidic monomers with phosphoric and/or carboxylic acid groups.

However, it was found that the respective acidic formulations sometimes inhibit the redox initiators of subsequently applied dual-cure or self-cure composite materials, especially if those contain a peroxide/amine redox initiator system.

This may lead to a poor cure of the dental composite at the interface, resulting in a low bond strength of the dental composite material to the dental adhesive and/or surface of hard dental tissue, respectively. This incompatibility issue is known, as e.g. described in the following publications:

F. R. Tay, D. H. Pashley, C. K. Y. Yiu, A. M. E. Sanares, S. H. Y. Wei: "Factors contributing to the incompatibility between simplified adhesives and chemically-cured or dual-cured composites. Part I. Single-step self-etching adhesive", J. Adhes. Dent. 2003, 5, 27-40;

F. R. Tay, B. I. Suh, D. H. Pashley, C. Prati, S.-F. Chuang, F. Li: "Factors contributing to the incompatibility between simplified-step adhesives and self-cured or dual-cured composites. Part II. Single-bottle, total-etch adhesive", J. Adhes. Dent. 2003, 5, 91-105;

B. I. Suh, L. Feng, D. H. Pashley, F. R. Tay: "Factors contributing to the incompatibility between simplified-step adhesives and chemically-cured or dual-cured composites. Part III. Effect of acidic resin monomers", J. Adhes. Dent. 2003, 5, 267-282;

A. M. E. Sanares, A. Itthagarun, N. M. King, F. R. Tay, D. H. Pashley: "Adverse surface interactions between one-bottle light-cured adhesives and chemical-cured composites", Dent. Mater. 2001, 17, 542-556. To overcome this incompatibility, the use of so-called activators was suggested.

These activators contain additional redox-active components, like sulfinate salts, which have to be mixed with the adhesive composition before application to the dental hard tissue.

It is assumed that in an acidic environment, the sulfinate can form radicals which can aid in the initiation of polymerization (Scotchbond™ Multi-Purpose Plus-Technical Product Profile, 3M, 1994, p. 8).

However, due to the instability of sulfinates in the presence of acids, these activators have to be provided as separate components which either have to be mixed with the adhesive before or applied in a separate step.

Alternatively, they can be placed on a dental applicator, e.g. a brush or sponge as described in e.g. in U.S. Pat. No. 6,288,138 (Sun Medical), U.S. Pat. No. 6,450,717 (Ivoclar) or EP 2 412 361 (3M).

US 2003/050359 (Kimura et al) describes a dental adhesive composition comprising (A) a polymerizable monomer comprising an acidic-group containing polymerizable monomer such as 11-methacryloyloxy-1,1-undecane dicarboxylic acid, (B) a mixed filler of a spherical filler substantially consisting of a non-crosslinking polymethyl methacrylate and a spherical filler substantially consisting of a non-crosslinking polyethyl methacrylate; and (C) a polymerization initiator; and a dental adhesive kit comprising the above dental adhesive composition in combination with a dental primer comprising (D) an acidic-group containing polymerizable monomer, (E) an aryl borate, (F) an organosulfinic acid salt and (G) water. A different approach is described in US 2013/0018123 A1 (Liu et al.).

In this reference, a self-curing activator for chemical polymerization of the interface of a dental bonding agent and a self-curing or dual curing dental cement or restorative is described, which includes an aryl borate compound, a polymerizable monomer, an optional acidic compound, an amine compound which exhibits a catalytic action, an organic peroxide containing material, and a metal compound wherein said metal compound promotes the decomposition of the organic peroxide.

WO 2013/082337 A1 (Hecht et al.) relates to a one-part self-adhesive composition for dental use comprising radically polymerizable component(s) with an acidic moiety as component (A), radically polymerizable component(s) without an acidic moiety as component (B), an oxidizing agent comprising persulfate(s) as component (C), transition metal component(s) as component (D), photo-initiator system(s) as component (E), optionally non acid-reactive filler(s) as component (F), and optionally additive(s) as component (G).

US 2016/0051450 A1 (Kashiki et al.) relates to an adhesive kit comprising a pretreatment agent (B) comprising an acidic group-containing radical polymerizable monomer (b1), a polymerization accelerator (b2), a solvent (b3), and a hydrophilic radical polymerizable monomer (b4) having no acidic group; and a curable composition (A), wherein the polymerization accelerator (b2) is a vanadium compound (b2-1) and/or a copper compound (b2-2).

US 2010/0311864 (Arita et al.) describes a dental primer comprising (meth)acrylate having an acid group, water, a water-soluble volatile organic solvent, and a vanadium compound.

U.S. Pat. No. 5,847,025 (Moszner et al.) describes a light-curing composite material which is characterized by a content of anaerobic stabilizer and/or stable organic radicals and which is said to have a reduced light sensitivity and an improved vacuum stability and is therefore suitable in particular as a dental filling material.

WO 2015/051217 A1 (Dentsply) relates to dental composite compositions for reduced stress shrinkage that include a polymerizable resin, filler particles, and at least one polymerizable stable radical.

U.S. Pat. No. 8,501,834 (Maletz et al.) describes a dual cure, multicomponent dental composition, which contains a photopolymerizable monomer, a photo initiator, a molecular weight regulator, a polymerization inhibitor for increasing the storage stability, an inorganic filler and an initiator for chemical curing.

U.S. Pat. No. 6,552,140 B1 (Kneafsey et al.) describes an air-activatable polymerizable composition useful in the field of adhesion, sealants, surface coatings, moulding resins and composite materials. The composition comprises a) at least one free-radically polymerizable monomer, b) an activator system comprising at least one auto-oxidizable compound which is a beta diketone, c) soluble ionic transition metal salts and d) a weak or a latent weak acid, with the proviso that the composition does not contain a peroxide or any ingredient which is a significant source of radicals in the absence of air.

JP 2014/231493 A1 (Tokuyama) relates to a dental restoration kit consisting of a pretreatment agent and a dental restoration material for adhesion and fixation of the dental restoration material to a tooth cavity. The pretreatment agent contains an acidic monomer, water, a water-soluble solvent, one component of a chemical polymerization initiator and a radical chain transfer agent. The restoration material contains a non-acidic monomer, an inorganic filler, the other component of the chemical polymerization initiator and a photopolymerization initiator. The chemical polymerization initiator is formed by a fourth period transition metal compound and an organic peroxide.

SUMMARY

There is still a need for a dental adhesive composition which can be used for securely adhering of self-cure or dual-cure composite material to the surface of hard dental tissue, in particular, self-cure or dual-cure dental composite materials which contain a redox-initiator system comprising an oxidizing component (e.g. peroxide) and a reducing component (e.g. amine).

Ideally, the dental adhesive composition should be sufficiently storage stable, also with respect to colour stability, if possible.

If possible, the use of the dental adhesive composition should simplify the dental restorative procedure, e.g. by reducing the number of components and/or procedural steps needed for fixing a dental restorative composition or material to hard dental tissue.

One or more of the above objects are addressed by the invention described in the present text and the claims.

In one embodiment, the invention features a one-part dental adhesive composition as described in the present text and claims comprising
  polymerizable component(s) with an acidic moiety as Component A, preferably in an amount of 3 to 20 wt. %,
  photo-initiator(s) as Component B1, preferably in an amount of 0.5 to 2 wt. %, transition metal ion component(s) as Component C, preferably in an amount of 0.01 to 1 wt. %,
  optionally solvent(s) other than water as Component D1, preferably in an amount of 5 to 40 wt. %, water as Component D2, preferably in an amount of 1 to 30 wt. %,
  a stabilizer as Component E, the stabilizer comprising a free radical moiety or being selected from anaerobic stabilizers, preferably in an amount of 0.01 to 0.5 wt. %,
for use in a process of fixing a self-cure or dual-cure dental composite material to the surface of hard dental tissue, the self-cure or dual-cure composite material comprising a redox initiator system with an oxidizing agent and a reducing agent.

In another embodiment, the invention relates to a kit of parts as described in the present text and claims comprising the dental adhesive composition described in the present text and a self-cure dental composite material, the self-cure composite material comprising polymerizable component(s) without an acidic moiety, filler(s) and a redox-initiator system comprising an oxidizing agent and a reducing agent.

Unless defined differently, for this description the following terms shall have the given meaning:

The term "compound" is a chemical substance which has a particular molecular identity or is made of a mixture of such substances, e.g., polymeric substances.

A "derivative" or "structural analogue" is a chemical compound showing a chemical structure closely related to the corresponding reference compound and containing all featured structural elements of the corresponding reference compound but having small modifications like bearing additional chemical groups like e.g. alkyl moieties, Br, Cl, or F or not bearing chemical groups like e.g. alkyl moieties in comparison to the corresponding reference compound. That is, a derivative is a structural analogue of the reference compound. A derivative of a chemical compound is a compound comprising the chemical structure of said chemical compound.

A "dental composition" or a "composition for dental use" or a "composition to be used in the dental field" is any composition which can and is to be used in the dental field. In this respect, the composition should be not detrimental to the patients' health and thus free of hazardous and toxic components being able to migrate out of the composition.

Dental compositions are typically hardenable compositions, which can be hardened at ambient conditions, including a temperature range from 15 to 50° C. or from 20 to 40° C. within a time frame of 30 min or 20 min or 10 min. Higher temperatures are not recommended as they might cause pain to the patient and may be detrimental to the patient's health.

Dental compositions are typically provided to the practitioner in rather small volumes, that is volumes in the range from 0.1 to 100 ml or from 0.5 to 50 ml or from 1 to 30 ml. Thus, the storage volume of useful packaging devices is within these ranges.

"One component or part" means that all components of the composition are present in the composition during storage and use. That is, the composition to be applied or used is not prepared by mixing different parts of the composition before use. In contrast to one-part compositions, those compositions are often referred to as two-component compositions (e.g. being formulated as powder/liquid, liquid/liquid or paste/paste compositions.

A "polymerizable component" is any component which can be cured or solidified e.g. by heating to cause polymerization or chemical crosslinking, or e.g. by radiation-induced polymerization or crosslinking, or e.g. using a redox initiator or by any other radical forming process. A radically polymerizable component may contain only one, two, three or more radically polymerizable groups. Typical examples of radically polymerizable groups include unsaturated carbon groups, such as a vinyl group being present e.g. in a (meth)acrylate group.

A "monomer" is any chemical substance which can be characterized by a chemical formula, bearing radically polymerizable unsaturated groups (including (meth)acrylate groups) which can be polymerized to oligomers or polymers thereby increasing the molecular weight. The molecular weight of monomers can usually simply be calculated based on the chemical formula given.

"Polymer" or "polymeric material" are used interchangeably to refer to a homopolymer, copolymer, terpolymer etc.

As used herein, "(meth)acryl" is a shorthand term referring to "acryl" and/or "methacryl". For example, a "(meth)acryloxy" group is a shorthand term referring to either an acryloxy group (i.e., $CH_2=CH-C(O)-O-$) and/or a methacryloxy group (i. e., $CH_2=C(CH_3)-C(O)-O-$).

An "ethylenically unsaturated acidic compound" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, phosphonic acid residues or sulfonic acid residues, such as —$SO_3H$.

A "solvent" means a liquid which is able to at least partially disperse or dissolve a component at ambient conditions (e.g. 23° C.). A solvent typically has a viscosity below about 5 or below about 1 or below about 0.1 Pa*s.

As used herein, "hardening" or "curing" a composition are used interchangeably and refer to polymerization and/or crosslinking reactions including, for example, photopolymerization reactions and chemical polymerization techniques (e. g., ionic reactions or chemical reactions forming radicals effective to polymerize ethylenically unsaturated compounds) involving one or more materials included in the composition.

A "self-cure dental composite material" means a material which can harden without applying radiation. Such a material typically contains a redox-initiator system comprising an oxidizing component (such as a peroxide) and a reducing component (such as an amine). During storage a self-cure dental composite material is typically provided as a kit of parts where the components of the redox-initiator system are separated from each other.

A "dual-cure dental composite material" means a self-cure dental composite material which contains in addition a photo-initiator system.

As used herein, a "dental surface" or "dental hard tissue" refers to tooth structures (e. g., enamel, dentin, and cementum) and bone.

A "dental restoration" refers to a material or means for restoring the function of missing tooth structure. Examples of dental restorations include dental filling materials, provisional crown and bridge materials, dental crowns and bridges, inlays, onlays, veneers, root canal fillers and dental posts.

A "self-etching composition" refers to a composition which bonds to a dental surface without pre-treating the dental surface with an etchant. Preferably, a self-etching composition can also function as a self-adhesive primer wherein no separate etchant or primer is used or be a self-adhesive composition.

A "self-adhesive composition" refers to a composition that is capable of bonding to a dental surface without pre-treating the dental surface with a primer or bonding agent. Preferably, a self-adhesive composition is also a self-etching composition wherein no separate etchant is used.

An "untreated dental surface" refers to a tooth or bone surface that has not been treated with an etchant, primer, or bonding agent prior to application of a self-etching adhesive or a self-adhesive composition. However, it may have been treated mechanically with a dental bur, grinding or polishing media, pumice etc.

An "unetched" dental surface refers to a tooth or bone surface that has not been treated with an etchant prior to application of a self-etching adhesive or a self-adhesive composition.

A "functionalised silane compound" is a silane compound bearing one or more moieties, which is able to undergo chemical reactions beyond condensation with OH-moieties of other silanes or on the surface of a filler. Examples of functionalised silane compounds include amino or (meth)acrylate functionalised silanes, like 3-aminopropyl trimethoxysilane or 3-(meth)acryloxypropyl trimethoxysilane.

A "non-surface treated filler" in the context of the invention is a filler having a surface which has not been exposed to reactive substances resulting in a modification of the surface of the filler to make the filler more compatible with other components of the composition.

"Ambient conditions" mean the conditions which the composition described in the present text is usually subjected to during storage and handling. Ambient conditions may, for example, be a pressure of 900 to 1100 mbar, a temperature of 10 to 40° C. and a relative humidity of 10 to 100%. In the laboratory, ambient conditions are typically adjusted to 20 to 25° C. and 1000 to 1025 mbar.

A material or composition is "essentially or substantially free of" a certain component within the meaning of the invention, if the material or composition does not contain said component as an essential feature. Thus, said component is not wilfully added to the composition or material either as such or in combination with other components or ingredient of other components. A composition or material being essentially free of a certain component usually contains the component in an amount of less than 1 wt. % or less than 0.1 wt. % or less than 0.01 wt. % with respect to the whole composition or material. Ideally the composition or material does not contain the said component at all. However, sometimes the presence of a small amount of the said component is not avoidable e.g. due to impurities.

As used herein, "a" "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and used in the specification and claims are to be understood as number as such and also as being modified by the term "about."

The term "about" can allow for a degree of variability in a value or range, e.g. within 10% or within 5% or within 1% of a given value or a given limit of a range.

The terms "comprise" or "contain" and variations thereof do not have a limiting meaning where these terms appear in the description and claims. The term "comprise" shall include also the terms "consist essentially of" and "consist of".

"And/or" means one or both. E.g., the expression component A and/or component B refers to a component A alone, component B alone, or to both component A and component B.

DETAILED DESCRIPTION

It has been found that the composition described in the text has a couple of advantageous properties.

Surprisingly it was found that a one-part dental adhesive composition showing high bond strength with redox-curing composite materials can be obtained, if a transition metal component is added to an acidic dental adhesive formulation.

This enables a simplified procedure for adhesively fixing a self-cure dental composite material to hard dental tissue.

If the dental adhesive composition described in the present text is used, there is no need for a device or applicator with a separately stored activator component any longer.

The present invention allows the formulation of a one-part dental adhesive composition without the need of adding or providing in a separate part a sulfinic acid component to address the possible incompatibility issue if an acidic dental adhesive formulation is combined with a self- and dual-cure composite material.

The dental practitioner now can conduct a dental restoration procedure with less inventory and more efficiently.

If a one-part dental adhesive composition is desired, which in addition to high bond strength also shows improved storage stability, the use of certain stabilizer components is suggested.

The addition of a transition metal salt to the one-part dental adhesive composition may reduce the storage-stability of the adhesive formulation.

Without wishing to be bound to a particular theory, it is assumed that the transition metal ion may catalyze the decomposition of peroxy radicals present in the formulation (reaction products of monomers and ambient oxygen). The resulting reactive radicals can initiate premature polymerization and thus reduce shelf life.

However, simply increasing the amount of commonly used stabilizers like BHT (butylated hydroxytoluene) or MEHQ (hydroquinone monomethyl ether) did not solve this issue, as in some cases, the shelf life was still not sufficient.

Further, in some cases, the use of these stabilizers resulted in an undesired discoloration of the formulations over time.

The use of the stabilizers suggested in the present text in combination with transition metal component, however, was found to be suitable for solving one or more of the above-mentioned objects.

The dental adhesive composition described in the present text comprises a polymerizable component with an acidic moiety as Component (A).

The acidic group typically comprises one or more carboxylic acid or anhydride residues, such as —COOH or —CO—O—CO—, phosphoric acid residues, such as —O—P(O)(OH)OH, phosphonic acid residues or sulfonic acid residues, such as —SO$_3$H.

The polymerizable component having an acidic moiety can be represented by the following formula:

$A_nBC_m$

B being a backbone group, such as (i) linear or branched C$_1$ to C$_{12}$ alkyl, optionally substituted with OH, (ii) C$_6$ to C$_{12}$ aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH, A being an ethylenically unsaturated group attached to the backbone group, such as a (meth)acryloyl moiety, C being an acidic group attached to the backbone group, with m, n=1, 2, 3, 4, 5 or 6, wherein the acidic group comprises one or more carboxylic acid or anhydride residues, such as —COOH or —CO—O—CO—, phosphoric acid residues, such as —O—P(O)(OH)OH, phosphonic acid residues or sulfonic acid residues, such as —SO$_3$H.

Specific examples of ethylenically unsaturated acidic compounds include, but are not limited to glycerol phosphate mono(meth)acrylates, glycerol phosphate di(meth)acrylates, hydroxyethyl (meth)acrylate phosphates, bis glycerol phosphate di(meth)acrylates, bis((meth)acryloxyethyl) phosphate, ((meth)acryloxypropyl)phosphate, bis((meth)acryloxypropyl) phosphate, bis((meth)acryloxy)propyloxy phosphate, (meth)acryloxyhexylphosphate, bis((meth)acryloxyhexyl)phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, di or tri(meth)acrylated citric acid, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like.

The reaction products of (meth)acrylic acid with alkane diols (e.g. C$_2$ to C$_{20}$ or C$_2$ to C$_{12}$ or C$_6$ to C$_{10}$) and phosphorous oxide were found to be suitable as well.

Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Additionally, ethylenically unsaturated compounds with acid functionality include, for example, polymerizable bisphosphonic acids as disclosed for example in US 2004/0206932 A1 (Abuelyaman); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Fuchigami et al.) and EP 1 051 961 A1 (Hino et al.).

Typical compositions also include an ethylenically unsaturated acidic compound with at least one phosphoric acid group (e.g. P—OH moiety).

Examples of preferred phosphoric acid group-containing polymerizable monomer include 6-(meth)acryloxyhexyl dihydrogenphosphate, 7-(meth)acryloxyheptyl dihydrogenphosphate, 8-(meth)acryloxyoctyl dihydrogenphosphate, 9-(meth)acryloxynonyl dihydrogenphosphate, 10-(meth)acryloxydecyl dihydrogenphosphate, 11-(meth)acryloxyundecyl dihydrogenphosphate, 12-(meth)acryloxydodecyl dihydrogenphosphate, 16-(meth)acryloxyhexadecyl dihydrogenphosphate, 20-(meth)acryloxyeicosyl dihydrogenphosphate, bis[6-(meth)acryloxyhexyl]hydrogenphosphate, bis[8-(meth)acryloxyoctyl] hydrogenphosphate, bis[9-(meth)acryloxynonyl] hydrogenphosphate, bis[10-(meth)acryloxydecyl] hydrogenphosphate, 1,3-di(meth)acryloxypropyl dihydrogenphosphate, 2-(meth)acryloxyethylphenyl hydrogenphosphate, 2-(meth)acryloxyethyl-2-bromoethyl hydrogenphosphate, (5-methacryloxy)pentyl-3-phosphonopropionate, (6-methacryloxy)hexyl-3-phosphonopropionate, (10-methacryloxy)decyl-3-phosphonopropionate, (6-methacryloxy)hexyl-3-phosphonoacetate, (10-methacryloxy)decyl-3-phosphonoacetate, 2-methacryloxyethyl (4-methoxyphenyl) hydrogenphosphate and 2-methacryloxypropyl (4-methoxyphenyl) hydrogenphosphate and mixtures thereof.

Mixtures of different Components A can be used, if desired.

The polymerizable component with an acidic moiety is typically present in the following amount(s):
  Lower limit: at least 1 or at least 2 or at least 3 wt. %;
  Upper limit: utmost 30 or utmost 25 or utmost 20 wt. %;
  Range: 1 to 30 or 2 to 25 or 3 to 20 wt. %;
  wt. % with respect to the whole amount of the composition.

The dental adhesive composition described in the present text comprises one or more photo-initiator(s) as Component B1.

The nature and structure of the photo-initiator is not particularly limited unless the intended purpose is not negatively affected.

Suitable photo-initiator(s) for free radical polymerization are generally known to the person skilled in the art dealing with dental materials.

As photo-initiator(s), those which can polymerize the polymerizable monomer(s) by the action of visible light having a wavelength of from 350 nm to 500 nm are preferred.

Suitable photo-initiator(s) often contain an alpha-alpha di-keto moiety, an anthraquinone moiety, a thioxanthone moiety or benzoin moiety. Photo-initiator(s) containing an alpha-alpha di-keto moiety are often preferred.

Examples of photo-initiator(s) include camphorquinone, 1-phenyl propane-1,2-dione, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthra-quinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylaminobenzophenone.

The photo-initiator is typically present in the following amount(s):
  Lower limit: at least 0.1 or at least 0.2 or at least 0.5 wt. %;
  Upper limit: utmost 4 or utmost 3 or utmost 2 wt. %;
  Range: 0.1 to 4 or 0.2 to 3 or 0.5 to 2 wt. %;
  wt. % with respect to the whole amount of the dental adhesive composition.

The dental adhesive composition described in the present text may also comprise reducing agent(s) as Component B2.

As reducing agent(s) amines, in particular secondary and tertiary amines can be used. Tertiary amines are sometimes preferred.

Suitable examples include triethanolamine, diethanolamine, methyl diethanolamine, 2-dimethylaminoethyl (meth)acrylate, 3-dimethylaminopropyl (meth)acrylate, 4-dimethylaminobutyl (meth)acrylate, 6-dimethylaminohexyl (meth)acrylate, 10-dimethylaminodecyl(meth)acrylate, 4-dimethylaminophenetylalcohol, 4-diethylaminophenetyl alcohol, 4-dipropylaminophenetyl alcohol, N,N-di(2-hydroxyethyl)-p-toluidine, N,N-di(2-hydroxypropyl)-p-toluidine, N,N-dimethyl-p-toluidine, N,N-dipropyl-p-toluidine, N,N-diethyl-p-toluidine, N,N-diethoxyethyl-p-toluidine, N,N-dibutoxyethyl-p-toluidine, N,N-di(polyoxyethylene)oxyethyl-p-toluidine, hexamethylenediamine, a dimethylamine aqueous solution, pentamethylenediamine, diethylamine, ethylenediamine, 2-aminoethanol, triethylamine and 2-dimethylaminoethanol.

In particular the following amines were found to be useful: N,N-dimethylaminoethyl methacrylate, ethyl 4-dimethylaminobenzoate, methyl 4-dimethylaminobenzoate, triethanolamine, N,N-dimethyl-p-toluidine, N,N-di-2-hydroxyethyl-p-toluidine, and isoamyl 4-dimethylaminobenzoate.

The reducing agent(s), if present, is typically present in the following amount(s):
  Lower limit: at least 0.1 or at least 0.3 or at least 0.5 wt. %;
  Upper limit: utmost 4 or utmost 3 or utmost 2 wt. %;
  Range: 0.1 to 4 or 0.3 to 3 or 0.5 to 2 wt. %;
  wt. % with respect to the whole amount of the dental adhesive composition.

The dental adhesive composition described in the present text contains transition metal component(s) as Component C.

The nature and structure of the transition metal component(s) is not particularly limited, unless the desired result cannot be achieved.

Suitable transition metal component(s) include organic and/or inorganic salt(s) from vanadium, chromium, manganese, iron, cobalt, nickel, and/or copper, with copper, iron and vanadium being sometimes preferred.

According to one embodiment, the transition metal component is a copper containing component.

The oxidation stage of copper in the copper containing component(s) is preferably +1 or +2.

Typical examples of copper component(s) which can be used include salts and complexes of copper including copper acetate, copper chloride, copper benzoate, copper acetylacetonate, copper naphthenate, copper carboxylates, copper bis(1-phenylpentan-1,3-dione) complex (copper procetonate), copper salicylate complexes of copper with thiourea, ethylenediaminetetraacetic acid and/or mixtures thereof. The copper compounds can be used in hydrated form or free of water. Especially preferred is copper(II) acetate.

According to one embodiment, the transition metal component is an iron containing component.

The oxidation stage of iron in the iron containing component(s) is preferably +2 or +3.

Typical examples of iron containing component(s) which can be used include salts and complexes of iron including Fe(III) sulfate, Fe(III) chloride, iron carboxylates, iron naphthenate, Fe(III) acetylacetonate including the hydrates of these salts.

According to one embodiment, the transition metal component is a vanadium containing component.

The oxidation stage of vanadium in the vanadium containing component(s) is preferably +4 or +5.

Typical examples of vanadium component(s) which can be used include salts and complexes of vanadium including vanadium acetylacetonate, vanadyl acetylacetonate, vanadyl stearate, vanadium naphthenate, vanadium benzoyl acetonate, vanadyl oxalate, bis(maltolato)oxovanadium (IV), oxobis(1-phenyl-1,3-butanedionate)vanadium (IV), vanadium (V) oxytriisopropoxide, ammon metavanadate (V), sodium metavanadate (V), vanadium pentoxide (V), divanadium tetraoxide (IV), and vanadyl sulfate (IV) and mixtures thereof, with vanadium acetylacetonate, vanadyl acetylacetonate, and bis(maltolato)oxovanadium (IV) being sometimes preferred.

The transition metal component(s) is typically present in the following amount:
Lower limit: at least 0.001 or at least 0.005 or at least 0.01 wt. %;
Upper limit: utmost 1 or utmost 0.8 or utmost 0.5 wt. %;
Range: 0.001 to 1 or 0.005 to 0.8 or 0.01 to 0.5 wt. %;
wt. % with respect to the whole composition.

The dental adhesive composition described in the present text may also comprise solvent(s) other than water as Component D1.

Adding solvent(s) or co-solvent(s) may help to adjust the viscosity and consistency of the composition.

Examples of solvents include, but are not limited to linear, branched or cyclic, saturated or unsaturated alcohols, ketones, esters, ethers or mixtures of two or more of said type of solvents with 2 to 10 C atoms. Preferred alcoholic solvents include methanol, ethanol, iso-propanol and n-propanol.

Other suitable organic solvents are THF, acetone, methylethyl ketone, cyclohexanol, toluene, alkanes and acetic acid alkyl esters, in particular acetic acid ethyl ester.

It is possible to use the above-mentioned solvents alone or as a mixture of two or more of any of these solvents, if the solvent mixtures do not impair the adhesive properties to such an extent that the desired result cannot be obtained.

If present, the solvent(s) is typically present in the following amount(s):
Lower limit: at least 5 or at least 8 or at least 10 wt. %;
Upper limit: utmost 40 or utmost 30 or utmost 20 wt. %;
Range: 5 to 40 or 8 to 30 or 10 to 20 wt. %;
wt. % with respect to the amount of the dental adhesive composition.

The dental adhesive composition described in the present text also comprises water as Component D2.
Water is typically provided in the form of de-ionized water.
Water may be present in the following amount(s):
Lower limit: at least 1 or at least 3 or at least 5 wt. %;
Upper limit: utmost 30 or utmost 25 or utmost 20 wt. %;
Range: 1 to 30 or 3 to 25 or 5 to 20 wt. %;
wt. % with respect to the whole amount of the composition.

The dental adhesive composition described in the present text also comprises one or more stabilizer(s) as Component E.

Adding a stabilizer may help to improve the storage stability of the dental adhesive composition, in particular the storage stability of a dental adhesive composition comprising a transition metal ion component.

Stabilizers which were found to be useful include those which comprise a free radical moiety or being selected from anaerobic stabilizers.

Free radical moieties include the moieties of
2,2-diphenyl-1-picrylhydrazyl (DPPH),
4-hydroxy-2,2,6,6-tetramethyl-piperidine 1-oxyl (TEMPOL),
2,2,6,6 Tetramethyl-piperidinyloxyl (TEMPO)
2,6-di-tert-butyl-α-(3,5-di-tert-butyl-4-oxo-2,5-cyclohexadien-1-ylidene)-p-tolyloxyl (Galvinoxyl),
triphenylmethyl radical.

Stabilizers comprising as free radical moiety the structural moiety of TEMPOL or TEMPO are sometimes preferred. If desired, these stabilizers can be characterized by either of the following formulas:

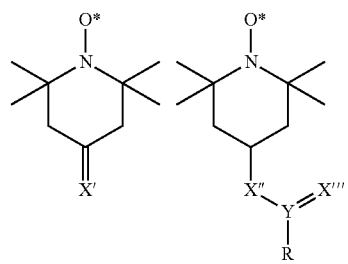

wherein X', X'', X''', Y and R independently or each other have the following meanings:
X'=O, S
X'', X'''=O, S or not present
Y=C or not present
R=H or alkyl, alkenyl, aryl, alkylaryl or arylalkyl having 1 to 12 C atoms each.

In particular, the following stabilizers were found to be useful: 4-hydroxy-2,2,6,6-tetramethylpiperidine 1-oxyl (Prostab™ 5198), bis(2,2,6,6-tetramethylpiperidin-1-oxyl-4-yl) decanedioate (Prostab™ 5415), 4-methacryloyloxy-2,2,6,6-tetramethylpiperidine-1-oxyl, 4-amino-2,2,6,6-tetramethylpiperidine-1-oxyl, 4-acetamido-2,2,6,6-tetramethylpiperidine-1-oxyl, 4-oxo-2,2,6,6-tetramethylpiperidine-1-oxyl, 2,2-diphenyl-1-picrylhydrazyl (DPPH), 2,2-Di(4-tert-octylphenyl)-1-picrylhydrazyl and mixtures thereof.

Stabilizers which are classified as anaerobic stabilizers typically comprise a phenothiazine moiety. If desired, these stabilizers can be characterized by the following formula:

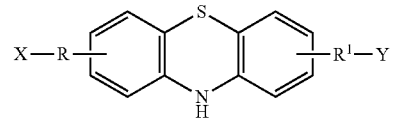

in which R, $R^1$, X, Y, $R^2$, $R^3$, $R^4$, $R^5$, $R^6$ and $R^7$, independently of each other, have the following meanings:
R and $R^1$=$C_1$ to $C_5$ alkylene or $C_1$ to $C_5$ oxyalkylene or $C_6$ to $C_{12}$ arylene, X and Y=H, halogen, $NO_2$, $NH_2$, $NR^2R_3$, OH, $OR^4$, CN, CHO, CO—$R^5$, COOH, CO—$NH_2$, CO—OR, $CH_2$=CH—, $CH_2$=CH—CO—, $CH_2$=C($CH_3$)—CO—, SH or S—$R^7$, $R^2$ to $R^7$=alkyl, alkenyl, aryl, alkylaryl or arylalkyl having in each case 1 to 12 C atoms.

In particular the following phenothiazine components were found to be useful: phenothiazine, alkyl- and halo substituted phenothiazines and mixtures thereof.

On the other hand, the following stabilizers were found to be less useful:

Butylated hydroxy toluene (BHT), hydroquinone, hydroquinone monomethyl ether (MEHQ), tris(2,4-ditert-butylphenyl)phosphite (Irgafos™ 168), 4,6-bis (dodecylthiomethyl)-o-cresol (Irganox™ 1726), 4,6-bis (octylthiomethyl)-o-cresol (Irganox™ 1520 L), octadecyl-3-(3,5-di-tert.butyl-4-hydroxyphenyl)-propionate (Irganox™ 1076), thiodiethylene bis[3-(3,5-di-tert-butyl-4-hydroxyphenyl)propionate](Irganox™ 1035), didodecyl 3,3'-thiodipropionate (Irganox™ PS 800 FL), 2',3-bis [[3-[3,5-di-tert-butyl-4-hydroxyphenyl]propionyl]]propionohydrazide (Irganox™ MD 1024), NOR-HALS like Flamestab™ NOR 116 FF), 3,5-di-tert-butyl-4-hydroxyanisole (2,6-di-tert-butyl-4-ethoxyphenol), 2,6-di-tert-butyl-4-(dimethylamino) methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, and 2-(2'-hydroxy-5'-methacryloxyethylphenyl)-2H-benzotriazole.

Using a too high amount of these stabilizers might cause undesired discoloration during storage. However, these stabilizers can nevertheless be used in addition, if desired.

If present, stabilizer(s) are present in the following amount(s):
Lower limit: at least 0.01 or at least 0.1 or at least 0.2 wt. %;
Upper limit: utmost 5 or utmost 3 or utmost 2 wt. %;
Range: 0.01 to 5 or 0.1 to 3 or 0.2 to 2 wt. %;
wt. % with respect to the amount of the dental adhesive composition.

The dental adhesive composition described in the present text may also comprise one or more filler(s) as Component F.

Fillers may be selected from one or more of a wide variety of materials suitable for incorporation in compositions used for dental applications.

The filler(s) which may be used in the compositions of the present text is preferably finely divided. The filler(s) can have a unimodal or polymodal (e.g., bimodal) particle size distribution. Typically, the maximum particle size (the largest dimension of a particle, generally, the diameter) of the filler(s) is less than 20 μm, more typically less than 10 μm, and most preferably less than 5 μm. Typically, the average primary particle size of the filler(s) is less than 0.1 μm, and more typically less than 0.075 μm.

The filler(s) should be nontoxic and suitable for use in the mouth or a patient. The filler(s) can be radiopaque or radiolucent. The filler typically is substantially insoluble in water. The compositions may include a filler comprising an inorganic material.

Examples of suitable inorganic fillers are naturally occurring or synthetic materials including, but not limited to: quartz; glasses derived from, e.g., Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas). Pyrogenic or precipitated silica has been found to be particularly useful.

Suitable pyrogenic silica fillers typically have a specific surface area (BET) of 100 to 400 m²/g.

Examples of non-surface treated fillers which can be used include AEROSIL™, including "OX 50," "90", "130", "150", "200", "300", and "380" silicas (Evonik Industries AG, Essen, Germany), and Cab-O-Sil, including "LM-150", "M-5", "H-5", "EH-5" silicas (Cabot Corp., Tuscola, IL), and HDK™, including "S13", "V15", "N20", "T30", "T40" silicas (Wacker-Chemie AG, Munich, Germany), and Orisil™, including "200", "300", "380" silicas (Orisil, Lviv, Ukraine).

Suitable filler(s) also include nano-sized silica particles, nano-sized metal oxide particles, and combinations thereof. Nanofillers are described e.g. in US 2005/0252413 (Kangas et al.); 2005/0252414 (Craig et al.); and 2005/0256223 (Kolb et al.).

Other suitable fillers are disclosed in U.S. Pat. No. 6,387, 981 (Zhang et al.), U.S. Pat. No. 6,572,693 (Wu et al.) U.S. Pat. No. 6,730,156 (Windisch), U.S. Pat. No. 6,899,948 (Zhang) as well as WO 03/063804 (Wu et al.).

The surface of the filler particles can be pre-treated with a silane coupling agent in order to enhance the bond between the filler and the resin.

Silanes which can be used for a surface treatment are described in the text below.

If present, filler(s) are present in the following amount(s):
Lower limit: at least 0.01 or at least 0.1 or at least 0.2 wt. %;
Upper limit: utmost 5 or utmost 3 or utmost 2 wt. %;
Range: 0.01 to 5 or 0.1 to 3 or 0.2 to 2 wt. %;
wt. % with respect to the amount of the dental adhesive composition.

The dental adhesive composition described in the present text may also comprise other polymerizable, non-acidic component(s) as Component G.

Component H is typically an ethylenically unsaturated compound without acidic moiety(s).

Suitable polymerizable component(s) without acidic moiety(s) can be characterized by the following formula:

$$A_n B A_m$$

with A being an ethylenically unsaturated group attached to backbone B, such as a (meth)acryl moiety,
B being selected from (i) linear or branched $C_1$ to $C_{12}$ alkyl, (ii) $C_6$ to $C_{12}$ aryl, optionally substituted with other functional groups (e.g. OH), or (iii) organic group having 4 to 20 carbon atoms bonded to one another by one or more ether, ester, amide, urethane, carbonyl and/or sulfonyl linkages,
m, n being independently selected from 0, 1, 2, 3, 4, 5 or 6 with the proviso that n+m is greater 0, that is that at least one A group is present.

Such polymerizable materials include mono-, di- or polyacrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Röhm Plex™ 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, trimethylolpropane tri(meth)acrylate, 1,2,4-butanetriol tri (meth)acrylate, 1,4-cyclohexanediol di(meth)acrylate, pentaerythritol tri(meth)acrylate, pentaerythritol tetraacrylate, pentaerythritol tetramethacrylate, sorbitol hexa(meth)acrylate, bis[1-(2-(meth)acryloxy)]-p-ethoxyphenyldimethylmethane, bis[1-(3-methacryloxy-2-hydroxy)]-p-propoxyphenyldimethylmethane (BisGMA), bis[1-(3-methacryloxy)]-p-propoxyphenyldimethylmethane, dimethacrylates of ethoxylated bisphenol A with 2-10 ethoxy units (e.g. BisEMA-6) and trishydroxyethyl-isocyanurate trimethacrylate;

bis-acrylates and bis-methacrylates of polyethylene glycols of molecular weight 200-500, copolymerizable mixtures of acrylated monomers (see e.g. U.S. Pat. No. 4,652,274 (Boettcher et al.)), and acrylated oligomers (see e.g. U.S. Pat. No. 4,642,126 (Zador et al.)); and vinyl compounds such as styrene, diallyl phthalate, divinyl succinate, divinyl adipate and divinylphthalate;

polyfunctional (meth)acrylates comprising urethane, urea or amide groups.

Examples of polyether (meth)acrylates include dialkylene glycol mono(meth)acrylate, for example, diethylene glycol mono(meth)acrylate, triethylene glycol mono(meth)acrylate, tetraethylene glycol mono(meth)acrylate, polyethylene glycol mono(meth)acrylate, dipropylene glycol mono(meth) acrylate, polypropylene glycol mono(meth)acrylate, and the like.

The molecular weight of these compounds is typically less than 20,000 g/mol, particularly less than 15,000 g/mol and in particular less than 10,000 g/mol.

Further examples for polymerizable component(s) are the dimethycrylate and the diacrylate derived from tricyclodecane-dimethanol (mixture of isomers), reaction products of tricyclodecane-dimethanol with isocyanatoethyl (meth) acrylate, reaction products of tricyclodecane-diisocyanate with hydroxyethyl (meth)acrylate or hydroxypropyl (meth) acrylate, such as bis[3[4]-methacryl-oxymethyl-8(9)-tricyclo[5.2.1.0$^{2,6}$]decylmethyl triglycolate and urethane (meth) acrylates and di(meth)acrylates of bishydroxymethyltricyclo-(5.2.1.0$^{2,6}$)decane. These kind of methacrylic esters are described in U.S. Pat. No. 4,795,823 (Schmitt et al.).

Polymerizable monomers comprising a hydroxyl moiety can also be added.

Suitable compounds include 2-hydroxyethyl methacrylate (HEMA), 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, 1,2- or 1,3- and 2,3-dihydroxypropyl (meth)acrylate, 2-hydroxypropyl-1,3-di(meth)acrylate, 3-hydroxypropyl-1, 2-di(meth)acrylate, N-(meth)acryloyl-1,2-dihydroxypropylamine, N-(meth)acryloyl-1,3-dihydroxypropylamine, 1-phenoxy-2-hydroxypropyl (meth)acrylate, 1-naphthoxy-2-hydroxypropyl (meth)acrylate.

2-Hydroxyethyl (meth)acrylate, 2-hydroxypropyl (meth) acrylate and 2,3-dihydroxypropyl (meth)acrylate are sometimes preferred.

If desired, it is also possible to use brominated components, like those which are described in EP patent application 17200519.1. The content of this reference is herewith incorporated by reference.

If brominated components are desired, in particular, the components were found to be useful, which comprise an aromatic moiety selected from brominated resorcinol, catechol, tyrosol, benzoic acid, or phenol moieties.

Mixtures of two or more of these free radically polymerizable materials can be used, if desired.

If present, the polymerizable component without an acidic moiety is typically present in the following amount(s):
Lower limit: at least 5 or at least 10 or at least 20 wt. %;
Upper limit: utmost 60 or utmost 50 or utmost 40 wt. %;
Range: from 5 to 60 or from 10 to 50 or from 20 to 40 wt. %;

wt. % with respect to the amount of the dental adhesive composition.

The dental adhesive composition described in the present text may also comprise one or more functionalized organosilane(s) as Component H.

The nature and structure of the organosilanes is not particularly limited unless the intended purpose is not negatively affected.

A suitable organosilane composition may comprise (meth)acrylate functional silane(s), amino functional silane(s) or a mixture of both.

Suitable functionalized organosilane components include alkoxy silane(s), preferably a trialkoxy silane comprising a (meth)acrylate group and at least one group that can hydrolyse with water.

Typical embodiments can be characterized by the following formula:

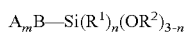

with A comprising a (meth)acryl moiety,
B comprising a spacer group, such as (i) linear or branched $C_1$ to $C_{12}$ alkyl, (ii) $C_6$ to $C_{12}$ aryl, (iii) organic group having 2 to 20 carbon atoms bonded to one another by one or more ether, thioether, ester, thioester, thiocarbonyl, amide, urethane, carbonyl and/or sulfonyl linkages,
$R^1$ comprising an alkyl group (e.g. $C_1$ to $C_6$) or an aryl group (e.g. $C_6$ to $C_{12}$), and
$R^2$ comprising an alkyl group (e.g. $C_1$ to $C_6$),
with m=1, 2, 3 or 4 and n=0, 1 or 2.

Examples of (meth)acrylate functionalized trialkoxy silanes include 3-(meth)acryloxypropyl trimethoxysilane, 3-(meth)acryloxypropyl triethoxysilane, 3-(meth)-acryloxypropyl tris(methoxyethoxy)silane, 3-(meth)acryloxypropenyl trimethoxysilane, (meth)acryloxyethyldimethyl(3-trimethoxysilylpropyl)ammonium chloride, N-(3-(meth) acryloxy-2-hydroxypropyl)-3-aminopropyltriethoxysilane, O-((meth)acryloxy-ethyl)-N-(triethoxysilylpropyl)urethane, (meth)acryloxymethyl trimethoxysilane, (meth)acryloxymethyl triethoxysilane, (meth)acryloxymethyl methyldimethoxysilane, (meth)acryloxymethyl methyldiethoxysilane, (meth)acryloxyoctyl trimethoxysilane, [(meth)acryloxymethyl]phenethyl trimethoxysilane, O-[(meth)acryloxyethyl]-N-(triethoxysilylpropyl)carbamate, (meth)acryloxypropyl triisopropoxysilane, (meth)acryloxypropyl methyldimethoxysilane, (meth)acryloxypropyl methyldiethoxysilane, 3-(meth)acryloxypropyl dimethylmethoxysilane, 3-(meth) acryloxypropyl dimethylethoxysilane, (meth)acryloxymethyl dimethylmethoxysilane, (meth)acryloxymethyl dimethylethoxysilane, oligomeric hydrolysate of 3-(meth) acryloxypropyl trimethoxysilane, oligomeric hydrolysate of 3-(meth)acryloxypropyl triethoxysilane.

The molecular weight of this component is typically within a range of 160 to 500 g/mol. These organosilane compounds may be used alone or admixtures thereof.

Amino functional silanes which can be used include 3-aminopropyl trimethoxysilane, 3-aminopropyl triethoxysilane, N-(2-aminoethyl)-3-aminopropyl trimethoxysilane, N-(2-aminoethyl)-3-aminopropyl triethoxysilane, N-cyclohexyl-3-aminopropyl trimethoxysilane, N-cyclohexyl-3-aminopropyl trimethoxysilane, 4-aminobutyl trimethoxysilane, 4-aminobutyl triethoxysilane, 4-amino-3,3-dimethylbutyl trimethoxysilane, 11-aminoundecyl triethoxysilane, 3-aminopropyl silanetriol, 4-amino-3,3-dimethylbutyl methyldimethoxysilane, 3-aminopropyl methyldimethoxysilane, 1-amino-2-(dimethylethoxysilyl)propane, 3-aminopropyl diisopropylethoxysilane, 3-aminopropyl dimethylethoxysilane, (aminoethylaminomethyl)phenethyl trimethoxysilane, N-(6-aminohexyl)aminomethyl triethoxysilane, N-(6-aminohexyl)aminopropyl trimethoxysilane, N-(2-aminoethyl)-11-aminoundecyl trimethoxysilane, N-3-[amino(poly-propylenoxy)]aminopropyl trimethoxysilane, N-(2-N-benzylaminoethyl)-3-aminopropyl trimethoxysilane, N-(2-aminoethyl)-3-aminopropyl silanetriol, N-(2-aminoethyl)-3-aminopropyl trimethoxysilane-propyl trimethoxysilane oligomers, N-(2-aminoethyl)-3-aminopropyl methyldimethoxysilane, N-(2-aminoethyl)-3-aminopropyl methyldiethoxysilane, N-(2-aminoethyl)-3-aminoisobutyl dimethylmethoxysilane, (3-trimethoxysilylpropyl)diethylenetriamine, 3-(N-allylamino)propyl trimethoxysilane, n-butylaminopropyl trimethoxysilane, t-butylaminopropyl trimethoxysilane, (N-cyclohexylaminomethyl) methyldiethoxysilane, (N-cyclohexylaminomethyl) triethoxysilane, (3-(N-ethylamino) isobutyl) methyldiethoxysilane, (3-N-(ethylamino)isobutyl) trimethoxysilane, N-methylaminopropyl methyldimethoxysilane, N-methylaminopropyl trimethoxysilane, (N-phenylaminomethyl) methyldimethoxysilane, N-phenylaminomethyl triethoxysilane, N-phenylaminopropyl trimethoxysilane, 1-[3-(2-aminoethyl)-3-aminoisobutyl]-1, 1,3,3,3-pentaethoxy-1,3-disilapropane, bis(methyldiethoxysilylpropyl)amine, bis(3-triethoxy-silylpropyl)amine, 1,11-bis(trimethoxysilyl)-4-oxa-8-azaundecan-6-ol, bis(3-trimethoxy-silylpropyl)amine, N,N'-bis[(3-trimethoxysilyl) propyl]ethylenediamine and mixtures thereof. The molecular weight of this component is typically within a range of 160 to 500 g/mol. These functionalized organosilane components may be used alone or admixtures thereof.

For improving the adhesion to certain ceramic surfaces (e.g. dental crowns) it can be advantageous, if a mixture of at least two organosilane components is used, e.g. an amino functional silanes and a (meth)acrylate functional silane.

If desired, the surface-treatment of the filler components can be done before the filler particles are combined with the other components of the dental composition.

Alternatively or in addition, the organosilane compounds can be added to the dental composition as a separate component or mixture of components.

In this case, typically an in-situ silanization takes place. Such a reaction is e.g. described in U.S. Pat. No. 7,968,617 B2 (Thalacker et al.). This reference is herewith incorporated by reference.

Non-surface treated fillers can be used as well and are sometimes preferred.

If present, the functionalized organosilane is present in the following amount(s):
  Lower limit: at least 1 or at least 3 or at least 5 wt. %;
  Upper limit: utmost 25 or utmost 20 or utmost 15 wt. %;
  Range: 1 to 25 or 3 to 20 or 5 to 15 wt. %;
  wt. % with respect to the amount of the dental adhesive composition.

The dental adhesive composition described in the present text may also comprise one or more additive(s) as Component I.

Additives of adjuvants which can be used include fluoride release agents, photobleachable colorants, dyes, and other ingredients well known to those skilled in the art. The amounts and types of each ingredient in the composition should be adjusted to provide the desired physical and handling properties before and after polymerization.

Examples of photobleachable colorants include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725 (Tom et al.). The colour of the compositions of the invention may be additionally imparted by a sensitizing compound.

Examples of fluoride release agents are naturally occurring or synthetic fluoride minerals such as sodium fluoride, simple and complex inorganic fluoride salts such as potassium zinc fluoride and potassium hexa fluorotitanate, simple and complex organic fluoride salts such as tetraethylammonium tetrafluoroborate or combinations thereof. These fluoride sources can optionally be treated with surface treatment agents.

If present, additive(s) are present in the following amount(s):
  Lower limit: at least 0.01 or at least 0.1 or at least 0.2 wt. %;
  Upper limit: utmost 5 or utmost 3 or utmost 2 wt. %;
  Range: 0.01 to 5 or 0.1 to 3 or 0.2 to 2 wt. %;
  wt. % with respect to the amount of the dental adhesive composition.

The dental adhesive composition described in the present text can typically be characterized by the following properties alone or in combination:
  a) viscosity: 0.01 to 3 Pa*s or 0.02 to 2 Pa*s at 23° C. and a shear rate of 100 s$^{-1}$;
  b) pH-value: 0.8 to 4, if determined with wet pH-sensitive paper;
  c) shear bond strength to dentin: at least 5 MPa or at least 9 MPa or at least 15 MPa;
  d) being radiation curable;
  e) being storage stable.

If desired, the respective properties can be determined as described in the example section.

A combination of the following properties is sometimes preferred: a) and b); a), b) and c); a), b), c) and d); a), b), c), and e).

That is, the composition described in the present text has a viscosity, which allows an easy application of the composition on the surface of a dental structure through a nozzle, e.g. using a syringe, brush or dropper bottle.

Further, the composition is acidic, i.e. it is able to etch the surface of a dental hard surface.

The composition is also storage stable, i.e. it remains a homogenous mixture during storage and use.

According to one embodiment, the composition contains the components in the following amounts:
  Component A (acidic monomers): 2 to 20 wt. %,
  Component B1 (photo-initiator): 0.1 to 3 wt. %,
  Component B2 (reducing agent): 0.1 to 3 wt. %,
  Component C (transition metal component): 0.01 to 0.5 wt. %,
  Component D1 (solvent): 0 to 40 wt. %,
  Component D2 (water): 1 to 20 wt. %,
  Component E (stabilizer): 0.01 to 0.5 wt.-%,
  Component G (non-acidic monomer): 0 to 40 wt. %,
  Component F (filler): 0 to 25 wt. %,
  Component H (functionalized silane): 0 to 10 wt.-%,
  Component I (additive): 0 to 5 wt. %,
  wt. % with respect to the weight of the whole composition.

According to another embodiment, the composition contains the components in the following amounts:
  Component A (acidic monomers): 2 to 20 wt. %,
  Component B1 (photo-initiator): 0.1 to 3 wt. %,
  Component B2 (reducing agent): 0.1 to 3 wt.-%, Component C (transition metal component): 0.01 to 0.1 wt.-%,
Component D1 (solvent): 5 to 40 wt. %,
Component D2 (water): 5 to 20 wt. %,
Component E (stabilizer): 0.01 to 0.1 wt.-%,
Component F (filler): 1 to 25 wt. %,
Component G (non-acidic monomer): 0 to 40 wt. %,
Component H (functionalized silane): 1 to 7 wt. %,
Component I (additive): 0 to 5 wt. %,
wt. % with respect to the weight of the whole composition.

According to a further embodiment, the composition contains the components in the following amounts:
Component A (acidic monomers): 2 to 20 wt. %,
Component B1 (photo-initiator): 0.1 to 3 wt. %,
Component B2 (reducing agent): 0.1 to 3 wt. %,
Component C (transition metal component): 0.01 to 0.07 wt. %,
Component D1 (solvent): 5 to 40 wt. %,
Component D2 (water): 5 to 20 wt. %,
Component E (stabilizer): 0.01 to 0.07 wt. %,
Component F (filler): 1 to 25 wt. %,
Component G (non-acidic monomer): 0 to 40 wt. %,
Component H (functionalized silane): 3 to 5 wt. %,
Component I (additive): 0 to 5 wt. %,
wt. % with respect to the weight of the whole composition.

According to a particular embodiment, the one-component dental adhesive composition comprises
polymerizable component(s) with an acidic moiety in an amount of 5 to 20 wt. %, photo-initiator(s) comprising an alpha-alpha diketo moiety in an amount of 0.5 to 3 wt. %,
transition metal ion component(s) selected from components comprising copper, iron or vanadium ions in an amount of 0.01 to 1 wt. %,
solvent(s) in an amount of 5 to 40 wt. %,
water in an amount of 5 to 20 wt. %,
reducing agent(s), in an amount of 0.1 to 3 wt. %,
stabilizer comprising a free radical moiety or being selected from anaerobic stabilizers, in an amount of 0.01 to 0.5 wt. %,
filler(s) comprising silica in an amount of 0.5 to 10 wt. %,
polymerizable component(s) without an acidic moiety in an amount of 5 to 60 wt. %,
functionalized silane comprising a (meth)acrylate moiety in an amount of 1 to 10 wt. %,
functionalized silane comprising an amino moiety in an amount of 1 to 10 wt. %,
additive(s) in an amount of 0 to 5 wt. %,
wt. % with respect to the weight of the dental adhesive composition, wherein the individual components are as described in the present text.

According to one embodiment, the dental adhesive composition described in the present text does typically not comprise (i.e. is essentially free of) the following components alone or in combination:
Sulfinic acid component(s), preferably in an amount of less than 0.1 wt. %;
Boron containing component(s), preferably in an amount of less than 0.1 wt. %;
Persulfate component(s), preferably in an amount of less than 0.1 wt. %;
Thiourea component(s), preferably in an amount of less than 0.1 wt. %;
Cysteine component(s), preferably in an amount of less than 0.1 wt. %;
wt. % with respect to the amount of the dental restorative composition.

Specific examples of sulfinic acid components which are typically not present in the dental adhesive composition include benzenesulfinic acid, sodium benzenesulfinate, sodium benzenesulfinate dihydrate, sodium toluenesulfinate, formamidinesulfinic acid, sodium salt of hydroxymethanesulfinic acid, sodium salt of 2,5-dichlorobenzenesulfinic acid, 3-acetamido-4-methoxybenzenesulfinic acid.

The composition described in the present text can be produced as follows: providing the components of the composition, mixing the components. The temperature at which the process can be conducted is not particularly limited.

The temperature used should be below the boiling point of the composition at normal pressure (1013 mbar). Usually the process can be conducted at a temperature in the range of 5° C. to 100° C. or within a range of 10° C. to 80° C. Conducting the process under ambient temperature (e.g. about 23° C.) has been found possible as well.

The atmosphere under which the process of the invention can be conducted is not particularly limited, either.

Usually, the processes are conducted under ambient conditions. Depending on the components used, conducting the process under inert conditions can be recommended. In this respect, a nitrogen or argon atmosphere could be useful.

The pressure under which the process of the invention can be conducted is not particularly limited, either. However, the process is typically conducted under ambient pressure (about 1013 mbar). The mixture should be stirred until a homogeneous dispersion or solution is obtained.

Depending on the process conditions, this can be accomplished within a few hours (e.g. at least 1 or at least 5 or at least 10 h) or a few days (e.g. at least 1 or at least 2 days). A time range within 2 to 20 h can be useful. The manner how the components are added is not particularly limited.

The composition is preferably mixed during its preparation. Mixing or dispersing of components can be accomplished using a device such as magnetic stirrers, mechanical stirrers, dissolvers, ball mills, attritor mills or high shear equipment.

For storage, the composition described in the present text is typically packaged in a suitable packaging device. The composition is provided as a one-part composition.

That is, all components of the composition are present together during storage and use. No mixing of different parts of the composition is required for application.

Suitable packaging devices include vials, bottles, blisters, syringes, foil pouches, and cartridges. If desired, the dental adhesive composition can also be provided in a single-use package.

Suitable vials are described e.g. in U.S. Pat. No. 5,996,796 (Kvitrud et al.), WO 2011/056814 A1 (3M) and EP application 17180193.9 (3M).

The dental adhesive composition may also be stored in a container formed by two sheets, interconnected by hot sealing and cooperating to form a compartment for receiving the liquid and a pocket for receiving a brush i.e. a blister. These kinds of devices are described e.g. in U.S. Pat. No. 6,105,761 (Peuker et al.).

The volume of the packaging device is typically in the range of 0.1 to 100 ml or 0.5 to 50 ml or 1 to 30 ml.

If the packaging device is intended for a single use only, the volume is typically in the range of 0.03 to 2 ml or 0.06 to 1 ml or 0.08 to 0.3 ml.

The invention also relates to a kit of parts comprising the dental adhesive composition as described in the present text and a self-cure or dual-cure dental composite material comprising a redox initiator system with an oxidizing agent (e.g. peroxide) and reducing agent (e.g. an amine).

If desired, this kit of parts may also comprise further parts in addition alone or in combination: dental filling composite; dental sealant; dental cement; dental core build-up material; dental milling blank; hydrofluoric acid etchant; instruction for use.

The self-cure or dual-cure dental composite material to be used in combination with the dental adhesive composition is a polymerizable composition comprising the redox-initiator system and polymerizable components without acidic moiety, typically together with filler(s).

These component(s) can be the same as those described above with respect to the dental adhesive composition.

Self-cure dental composite materials are typically provided in different shapes and for different applications including luting cements, core build-up materials or dental filling or restorative materials. Self-cure dental composite materials are known in the art.

Commercially available self-cure dental composite materials containing a redox initiator system with an amine and a peroxide are e.g. Concise™ (from 3M Oral Care), Adaptic™ (from Dentsply-Sirona) and Alphaplast™ (from DMG).

Commercially available dual-cure dental composites are e.g. RelyX™ ARC (from 3M Oral Care), RelyX™ Unicem (from 3M Oral Care), RelyX™ Ultimate (from 3M Oral Care), Calibra™ (from Dentsply-Sirona), Luxacore™ (from DMG), Rebilda™ (from Voco).

The self-cure dental composite material is typically provided as a kit of parts comprising a base part and a catalyst part, wherein one part contains the oxidizing agent and the other part contains the reducing agent.

Oxidizing agents which can be present include peroxides, peroxyesters, diacylperoxides, persulfates.

According to one embodiment, the organic peroxide is a di-peroxide, preferably a di-peroxide comprising the moiety $R_1$—O—O—$R_2$—O—O—$R_3$, with $R_1$ and $R_3$ being independently selected from H, alkyl (e.g. $C_1$ to $C_6$), branched alkyl (e.g. $C_1$ to $C_6$), cycloalkyl (e.g. $C_5$ to $C_{10}$), alkylaryl (e.g. $C_7$ to $C_{12}$) or aryl (e.g. $C_6$ to $C_{10}$) and $R_2$ being selected from alkyl (e.g. ($C_1$ to $C_6$) or branched alkyl (e.g. $C_1$ to $C_6$).

Examples of suitable organic diperoxides include 2,2-Di-(tert.-butylperoxy)-butane and 2,5-Dimethyl-2,5-di-(tert-butylperoxy)-hexane and mixtures thereof.

Other peroxides which are often described in the literature are diacyl peroxide(s), dialkyl peroxide(s) and peroxyester (s).

Examples of peroxyesters include alpha-cumylperoxyneodecanoate, t-butyl peroxypivarate, t-butyl peroxyneodecanoate, 2,2,4-trimethylpentylperoxy-2-ethyl hexanoate, t-amylperoxy-2-ethyl hexanoate, t-butylperoxy-2-ethyl hexanoate, di-t-butylperoxy isophthalate, di-t-butylperoxy hexahydroterephthalate, t-butylperoxy-3,3,5-trimethylhexanoate, t-butylperoxy acetate, t-butylperoxy benzoate and t-butylperoxymaleic acid.

Examples of diacyl peroxides include acetyl peroxide, benzoyl peroxide, decanoyl peroxide, 3,3,5-trimethylhexanoyl peroxide, 2,4-dichlorobenzoyl peroxide and lauroylperoxide.

Examples of dialkyl peroxides include di-t-butyl peroxide, dicumylperoxide, t-butylcumyl peroxide, 2,5-dimethyl-2,5-di(t-butylperpoxy)hexane, 1,3-bis(t-butylperoxyisopropyl)benzene and 2,5-dimethyl-2,5-di(t-butylperoxy)-3-hexane.

Reducing agents which can be present include amines, in particular secondary and tertiary amines, sulfinic acid components, ascorbic acid components, and thiourea derivatives.

Suitable examples of amines include triethanolamine, diethanolamine, methyl diethanolamine, 2-dimethylaminoethyl (meth)acrylate, 3-dimethylaminopropyl (meth)acrylate, 4-dimethylaminobutyl (meth)acrylate, 6-dimethylaminohexyl (meth)acrylate, 10-dimethylaminodecyl (meth) acrylate, 4-dimethylaminophenetyl alcohol, 4-diethylaminophenetyl alcohol, 4-dipropylaminophenetyl alcohol, N,N-di(2-hydroxyethyl)-p-toluidine, N,N-di(2-hydroxypropyl)-p-toluidine, N,N-dimethyl-p-toluidine, N,N-dipropyl-p-toluidine, N,N-diethyl-p-toluidine, N,N-diethoxyethyl-p-toluidine, N,N-dibutoxyethyl-p-toluidine, N,N-di(polyoxyethylene)oxyethyl-p-toluidine, hexamethylenediamine, a dimethylamine aqueous solution, pentamethylenediamine, diethylamine, ethylenediamine, 2-aminoethanol, triethylamine and 2-dimethylaminoethanol.

In particular the following amines can be useful: N,N-dimethylaminoethyl methacrylate, ethyl 4-dimethylaminobenzoate, methyl 4-dimethylaminobenzoate, triethanolamine, N,N-dimethyl-p-toluidine, N,N-di-2-hydroxyethyl-p-toluidine, and isoamyl 4-dimethylaminobenzoate.

Useful can also be tertiary aromatic amines, such as the N,N-bis-(hydroxyalkyl)-3,5-xylidines known from U.S. Pat. No. 3,541,068 (Taylor) as well as N,N-bis-(hydroxyalkyl)-3,5-di-t-butylanilines, in particular N,N-bis-([beta]-oxybutyl)-3,5-di-t-butylaniline as well as N,N-bis-(hydroxyalkyl)-3,4,5-trimethylaniline.

Examples of sulfinic acid components include benzenesulfinic acid, sodium benzenesulfinate, sodium benzenesulfinate dihydrate, sodium toluenesulfinate, formamidinesulfinic acid, sodium salt of hydroxymethanesulfinic acid, sodium salt of 2,5-dichlorobenzenesulfinic acid, 3-acetamido-4-methoxybenzenesulfinic acid.

Particularly suitable sulfinic acid component are sodium toluenesulfinate or sodium benzenesulfinate and their hydrates.

Examples of ascorbic acid components include those which are formed by reacting one or more of the hydroxyl functions of ascorbic acid with a carboxylic acid, in particular the $C_2$ to $C_{30}$ carboxylic acid, or salts of ascorbic acid and its esters.

Examples of thiourea components include 1-ethyl-2-thiourea, tetraethyl thiourea, tetramethyl thiourea, 1,1-dibutyl thiourea, 1,3-dibutyl thiourea, and polymerizable thioureas such as (meth)acryloxyalkyl thiourea, 1-allyl thiourea, 1,1-diallyl thiourea, 1,3-diallyl thiourea, 1-allyl-3-(2-hydroxyethyl)-2-thiourea, and 1-allyl-3-methyl thiourea, as described in US2003166740 (Mitra).

During storage the oxidizing agent is separated from the reducing agent. Before use, the two parts are mixed.

A suitable kit of parts may comprise
the one-part dental adhesive composition as described in the present text and a self-cure dental composite material,
the one-part dental adhesive composition comprising
polymerizable component(s) with an acidic moiety as Component A,
a photo-initiator(s) as Component B1 and
transition metal ion component(s) as Component C,
a stabilizer as Component E, the stabilizer comprising a free radical moiety or being selected from anaerobic stabilizers,
the self-cure dental composite material comprising
polymerizable component(s) without an acidic moiety, filler(s) and
a redox-initiator system comprising
an oxidizing agent such as a peroxide, peroxyesters, diacylperoxides, or persulfate component and
a reducing agent such as an amine, sulfinic acid, ascorbic acid or thiourea component,
wherein the individual components are as described in the present text.

Another suitable kit of parts may comprise
the one-part dental adhesive composition as described in the present text and a dual-cure dental composite material,
the one-part dental adhesive composition comprising
polymerizable component(s) with an acidic moiety as Component A,
a photo-initiator(s) as Component B1 and
transition metal ion component(s) as Component C,
solvent(s) other than water as Component D1,
water as Component D2,
a stabilizer as Component E, the stabilizer comprising a free radical moiety or being selected from anaerobic stabilizers,
the dual-cure dental composite material comprising
polymerizable component(s) without an acidic moiety, filler(s),
a photo-initiator being same or different as the photo-initiator contained in the one-part dental adhesive composition,
a redox-initiator system comprising
an oxidizing agent such as a peroxide, peroxyesters, diacylperoxides, or persulfate component and
a reducing agent such as an amine, sulfinic acid, ascorbic acid or thiourea component,
wherein the individual components are as described in the present text.

Another suitable kit of parts may comprise
the one-part dental adhesive composition as described in the present text and a dual-cure dental composite material,
the one-part dental adhesive composition comprising
polymerizable component(s) with an acidic moiety as Component A,
a photo-initiator(s) comprising an alpha-alpha diketone moiety as Component B1 and
a reducing agent comprising an amine moiety as Component B2
transition metal ion component(s) comprising copper, vanadium or iron as Component C,
solvent(s) other than water as Component D1,
water as Component D2,
a stabilizer as Component E, the stabilizer comprising a free radical moiety or being selected from anaerobic stabilizers,
the dual-cure dental composite material comprising
polymerizable component(s) without an acidic moiety, filler(s),
a photo-initiator being same or different as the photo-initiator contained in the one-part dental adhesive composition,
a redox-initiator system comprising
an oxidizing agent such as a peroxide, peroxyesters, diacylperoxides, or persulfate component and
a reducing agent such as an amine, sulfinic acid, ascorbic acid or thiourea component,
wherein the individual components are as described in the present text.

The self-cure or dual-cure dental composite material described in the present text is typically stored in a container until use. Depending on the formulation and the curing status, various containers can be used.

The self-cure or dual-cure dental composite material is typically provided in the form of a two-component system. Suitable two-component systems for storage include two-barrel cartridges or syringes.

Suitable two-component systems are described e.g. in US 2007/0090079 (Keller) or U.S. Pat. No. 5,918,772 (Keller et al.). The content of these documents with respect to the description of the vial or bottle is herewith incorporated by reference. Cartridges which can be used are also commercially available from SulzerMixpac AG (Switzerland).

The volume of each compartment of the two-barrel cartridges is typically in the range of 0.1 to 100 ml or 0.5 to 50 ml or 1 to 30 ml.

The volume ratio of compartment (I) to compartment (II) is typically within a range of 1:1 to about 10:1.

Static mixing tips which can be used for mixing the compositions contained in the compartments are described e.g. in US 2006/0187752 (Keller) or in U.S. Pat. No. 5,944,419 (Streif). The disclosure of these patents is herewith incorporated by reference. Mixing tips which can also be used are commercially available from SulzerMixpac AG (Switzerland).

The dental adhesive composition described in the present text is for adhesively fixing a self-cure dental composite material to dental hard tissue. The dental adhesive composition described in the present text is typically used as follows:

The dental adhesive composition is applied to the tooth surface, typically in an amount sufficient to etch and prime dental tissue.

In this respect, the following steps are generally applied:
a) applying the dental adhesive composition described in the present text to the surface of hard dental tissue, preferably using a brush or a sponge; if desired, the surface of the hard dental tissue can be an etched surface (e.g. with phosphoric acid) or a non-etched surface,
b) optionally dispersing the dental adhesive composition to a thin film, preferably using a stream of air,
c) optionally radiation curing of the dental adhesive composition, the radiation having a wave length typically in range of 350 nm to 500 nm, and
d) applying a self-cure dental composite material, e.g. selected from a dental luting cement a core-build up material, a dental restorative material or an orthodontic adhesive.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof. The following examples are given to illustrate the invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Viscosity

If desired, viscosity can be measured using a Physica MCR 301 Rheometer (Anton Paar, Graz, Austria) with a cone/plate geometry CP25-1 under controlled shear rate at 23° C. The diameter is 25 mm, the cone angle 1, and the separation between the cone tip and the plate 49 µm. The shear rate is ramped down logarithmically from 1000 s- to 1 s$^{-1}$, with a total of 23 data points being collected. The integration time for each data point is 10 sec.

pH-Determination

If desired, the pH can be determined by using a wet pH sensitive paper.

Particle Size Distribution

If desired, the particle size can be measured using a Malvern Mastersizer 2000 (Malvern Instruments, Malvern, Worcestershire, UK) light scattering instrument. The Mastersizer 2000 uses an integrated optical system to cover the range from 0.02 to 2000 µm. The mixtures to be analysed is added to the test chamber filled with isopropanol until an obscuration of approximately 8-15% is reached. No ultrasound is applied in order not to alter the particle size distributions. The raw data is processed with the instrument software using a refractive index of 1.459 and applying the Mie correction together with the Fraunhofer approximation, frequently used techniques known to the expert.

Assessment of Storage Stability 5 ml of the experimental formulations were filled into empty Scotchbond™ Universal vials (3M Oral Care) and stored in an oven at 50° C. Stability against premature polymerization was rated sufficient ("+") when the formulation had not hardened after 1 week of storage. If it hardened within one week, it was rated not sufficient ("−").

Shear Bond Strength (SBS) to Bovine Teeth

Preparation of Teeth. Bovine incisal teeth, free of soft tissue, were embedded in circular acrylic disks. The embedded teeth were stored in water in a refrigerator prior to use. In preparation for adhesive testing, the embedded teeth were ground to expose a flat enamel or dentin surface using 120-grit sandpaper mounted on a lapidary wheel. Further grinding and polishing of the tooth surface was done manually using 320-grit sandpaper. The teeth were continuously rinsed with water during the grinding process. The polished teeth were stored in deionized water and used for testing within 2 hours after polishing. The teeth were allowed to warm in a 36° C. oven to between room temperature (23° C.) and 36° C. before use.

Treatment of Teeth. An adhesive test sample was applied with a dental applicator brush over the entire surface of the prepared enamel or dentin surface. After leaving the adhesive undisturbed for 20 seconds, a stream of compressed air was blown on until the adhesive film did not move anymore. Then the adhesive was light cured for 10 seconds with a dental curing light (Elipar™ S10, 3M, light intensity: approx. 1200 mW/cm$^2$). A 2.5 mm thick Teflon mold with a hole approximately 4.7 mm in diameter was clamped to the embedded tooth such that the hole in the mold exposed part of the adhesively prepared tooth surface. Pastes A and B of Concise™ Orthodontic Bond (3M) were mixed according to the instructions. The mixture was filled into the hole such that the hole was completely filled, but not overfilled, and left to cure chemically to form a "button" that was adhesively attached to the tooth. Samples were stored at 36° C./100% relative humidity for 24 hours before testing.

Adhesive Bond Strength Testing. The adhesive strength of a cured test example was evaluated by mounting the assembly (described above) in a holder clamped in the jaws of Zwick Universal testing machine (Zwick Z010, Zwick GmbH, Ulm, Germany) with the polished tooth surface oriented parallel to the direction of pull. A loop of orthodontic wire (0.71 mm diameter) was placed around the composite button adjacent to the polished tooth surface. The ends of the orthodontic wire were clamped in the pulling jaw of the Zwick apparatus and pulled at a crosshead speed of 2 mm/min, thereby placing the adhesive bond in shear stress. The force in Newtons (N) at which the bond failed was recorded, and this number was converted to a force per unit area (MPa) using the known surface area of the button. Each reported value of adhesion to enamel or adhesion to dentin represents the average of 5 replicates.

| | Abbreviations |
|---|---|
| DIBROERMA | synthesis described in EP patent application 17200519.1; page 37 |
| HEMA | 2-hydroxyethyl methacrylate |
| BisGMA | Bisphenol A diglycidyl methacrylate |
| MDP | reaction products of methacrylic acid with 1,10-decanediol and phosphorous oxide (CAS 1207736-18-2) |
| VBCP | Copolymer of acrylic acid and itaconic acid with pendant methacrylate groups, synthesized according to Example 11 of U.S. Pat. No. 5,130,347 (Mitra) |
| EDMAB | ethyl 4-dimethylaminobenzoate |
| DMAEMA | 2-dimethylaminoethyl methacrylate |
| BHT | 3,5-di-tert-butyl-4-hydroxytoluene |
| MEHQ | 4-Methoxyphenol |
| Irgafos ™ 168 | tris(2,4-ditert-butylphenyl)phosphite |
| Irganox ™ 1035 | thiodiethylene bis[3-(3,5-di-tert-butyl-4-hydroxyphenyl)propionate] |
| Irganox ™ 1076 | octadecyl-3-(3,5-di-tert.butyl-4-hydroxyphenyl)-propionate |
| Irganox ™ 1726 | 4,6-bis (dodecylthiomethyl)-o-cresol |
| Irganox ™ MD 1024 | 2',3-bis [[3-[3,5-di-tert-butyl-4-hydroxyphenyl]propionyl]]propionohydrazide |
| Irganox ™ PS 800 FL | didodecyl 3,3'-thiodipropionate |
| Flamestab ™ NOR 116 FF | oligomeric NOR-HALS |
| Prostab ™ 5198 | 4-hydroxy-2,2,6,6-tetramethylpiperidine 1-oxyl |
| Prostab ™ 5415 | bis(2,2,6,6-tetramethylpiperidin-1-oxyl-4-yl) decanedioate |
| PTA | phenothiazine |
| DPPH | 2,2-diphenyl-1-picrylhydrazyl |
| CPQ | Camphorquinone |
| MPTES | 3-Methacryloxypropyl trimethoxysilane |
| MPTMS | 3-methacryloxypropyl trimethoxysilane |

| Abbreviations | |
|---|---|
| APTES | 3-Aminopropyltriethoxysilane |
| A200 | Aerosil ™ 200, available from Evonik AG |
| Water | De-ionized water |
| V acac | Vanadyl acetylacetonate |
| Consice ™ | Orthodontic chemical cure adhesive (3M Oral Care) |

The formulations shown in Table 1 below were prepared by mixing the ingredients in a beaker using a magnetic stirrer bar at 23° C. for 24 hours. The amounts are given in wt. %.

Formulations were tested for shear bond strength (SBS) to bovine dentin as described above.

TABLE 1

| | Examples Classification | | | | | | | |
|---|---|---|---|---|---|---|---|---|
| | 1 CE | 2 CE | 3 CE | 4 CE | 5 CE | 6 CE | 7 CE | 8 CE |
| BHT | 0.10 | 0.05 | | | | | | |
| MEHQ | | | 0.05 | | | | | |
| Irgafos 168 | | | | 0.20 | | | | |
| Irganox 1035 | | | | | 0.20 | | | |
| Irganox 1076 | | | | | | 0.20 | | |
| Irganox 1726 | | | | | | | 0.20 | |
| Irganox MD 1024 | | | | | | | | 0.20 |
| Irganox PS 800 FL | | | | | | | | |
| Flamestab NOR 116 | | | | | | | | |
| FF | | | | | | | | |
| Prostab 5198 | | | | | | | | |
| Prostab 5415 | | | | | | | | |
| PTA | | | | | | | | |
| DPPH | | | | | | | | |
| BisGMA | | 19.68 | 19.68 | | | | | |
| DIBROERMA | 30.15 | | | 30.11 | 30.11 | 30.11 | 30.11 | 30.11 |
| HEMA | 19.30 | 23.22 | 23.22 | 19.27 | 19.27 | 19.27 | 19.27 | 19.27 |
| Ethanol | 12.06 | 13.33 | 13.33 | 12.04 | 12.04 | 12.04 | 12.04 | 12.04 |
| Water | 10.05 | 11.28 | 11.28 | 10.04 | 10.04 | 10.04 | 10.04 | 10.04 |
| MDP | 13.97 | 15.90 | 15.90 | 13.95 | 13.95 | 13.95 | 13.95 | 13.95 |
| DMAEMA | | 0.71 | 0.71 | | | | | |
| EDMAB | 0.90 | 1.02 | 1.02 | 0.90 | 0.90 | 0.90 | 0.90 | 0.90 |
| CQ | 1.41 | 1.62 | 1.62 | 1.40 | 1.40 | 1.40 | 1.40 | 1.40 |
| VBCP | 2.01 | 2.04 | 2.04 | 2.01 | 2.01 | 2.01 | 2.01 | 2.01 |
| A 200 | 6.13 | 8.10 | 8.10 | 6.12 | 6.12 | 6.12 | 6.12 | 6.12 |
| MPTMS | | 3.00 | 3.00 | | | | | |
| MPTES | 3.22 | | | 3.21 | 3.21 | 3.21 | 3.21 | 3.21 |
| APTES | 0.70 | | | 0.70 | 0.70 | 0.70 | 0.70 | 0.70 |
| Cu(II) acetate | | 0.04 | 0.04 | 0.04 | 0.04 | 0.04 | 0.04 | 0.04 |
| V acac | | | | | | | | |
| sum | 100 | 100 | 100 | 100 | 100 | 100 | 100 | 100 |
| Shelf life, 50° C. | + | − | − | − | − | − | − | − |
| SBS, dentin, SE, 24 h/36° C., [MPa]; (SD) | 0 | 14.4 (5.6) | 13.3 (7.6) | n.d. | n.d. | n.d. | n.d. | n.d. |

| | 9 CE | 10 CE | 11 IE | 12 IE | 13 IE | 14 IE | 15 IE |
|---|---|---|---|---|---|---|---|
| BHT | | | | | | | |
| MEHQ | | | | | | | |
| Irgafos 168 | | | | | | | |
| Irganox 1035 | | | | | | | |
| Irganox 1076 | | | | | | | |
| Irganox 1726 | | | | | | | |
| Irganox MD 1024 | | | | | | | |
| Irganox PS 800 FL | 0.20 | | | | | | |
| Flamestab NOR 116 | | 0.20 | | | | | |
| FF | | | | | | | |
| Prostab 5198 | | | 0.05 | | | | 0.05 |
| Prostab 5415 | | | | 0.05 | | | |
| PTA | | | | | 0.05 | | |
| DPPH | | | | | | 0.05 | |

TABLE 1-continued

| | | | | | | | |
|---|---|---|---|---|---|---|---|
| BisGMA | | | | 19.68 | 19.68 | 19.68 | 19.68 |
| DIBROERMA | 30.11 | 30.11 | 30.71 | | | | |
| HEMA | 19.27 | 19.27 | 19.65 | 23.22 | 23.22 | 23.22 | 23.22 |
| Ethanol | 12.04 | 12.04 | 12.28 | 13.33 | 13.33 | 13.33 | 13.33 |
| Water | 10.04 | 10.04 | 8.19 | 11.28 | 11.28 | 11.28 | 11.28 |
| MDP | 13.95 | 13.95 | 14.23 | 15.90 | 15.90 | 15.90 | 15.90 |
| DMAEMA | | | | 0.71 | 0.71 | 0.71 | 0.71 |
| EDMAB | 0.90 | 0.90 | 0.92 | 1.02 | 1.02 | 1.02 | 1.02 |
| CQ | 1.40 | 1.40 | 1.43 | 1.62 | 1.62 | 1.62 | 1.62 |
| VBCP | 2.01 | 2.01 | 1.43 | 2.04 | 2.04 | 2.04 | 2.04 |
| A 200 | 6.12 | 6.12 | 6.24 | 8.10 | 8.10 | 8.10 | 8.10 |
| MPTMS | | | | 3.00 | 3.00 | 3.00 | 3.00 |
| MPTES | 3.21 | 3.21 | 3.28 | | | | |
| APTES | 0.70 | 0.70 | 1.54 | | | | |
| Cu(II) acetate | 0.04 | 0.04 | 0.04 | 0.04 | 0.04 | 0.04 | |
| V acac | | | | | | | 0.04 |
| sum | 100 | 100 | 100 | 100 | 100 | 100 | 100 |
| Shelf life, 50° C. | − | − | + | + | + | + | + |
| SBS, dentin, SE, 24 h/36° C., [MPa]; (SD) | n.d. | n.d. | 22.4 (2.8) | 11.8 (1.3) | 9.8 (5.7) | 15.4 (3.6) | 21.8 (3.4) |

SD: standard deviation;
n.d.: not determined, due to limited shelf-life;
CE: comparative example,
IE: inventive example Evaluation The addition of small amounts (in the range of a few 100 ppm) of a transition metal salt can overcome the incompatibility of the acidic formulation of the Comparative Example with a redox cure composite like 3M Concise™ Orthodontic Bond.

The storage stability of formulations according to the present invention can be improved by adding stabilizers. In particular stabilizers containing stable radical moieties or anaerobic stabilizers were found to be suitable.

What is claimed is:

1. A one-part dental adhesive composition comprising:
    polymerizable component(s) with an acidic moiety as Component A;
    photo-initiator(s) as Component B1;
    transition metal ion component(s) as Component C, the transition metal ion component(s) present in a total amount of 0.001 wt % to 1 wt %;
    water as Component D2;
    a stabilizer as Component E, the stabilizer comprising a free radical moiety;
    optionally, a stabilizer selected from butylated hydroxy toluene, monomethyl ether hydroquinone, or a combination thereof, present in an amount of less than 0.01 wt % with respect to the weight of the one-part dental adhesive composition.

2. A method for fixing a dental composite material to a surface of hard dental tissue, the method comprising the steps of:
    applying a one-part dental adhesive composition of claim 1 to the surface of hard dental tissue,
    optionally applying radiation to the one-part dental adhesive composition,
    applying the dental composite material to the surface of hard dental tissue which has been treated with the one-part dental adhesive composition.

3. The one-part dental adhesive composition according to claim 1,
    the transition metal ion component(s) comprising metal ions selected from copper, iron or vanadium and mixtures thereof,
    and being present in an amount of 0.01 to 1 wt. % with respect to the weight of the dental adhesive composition.

4. The one-part dental adhesive composition according to claim 1,
    the photo-initiator(s) being selected from components comprising an alpha-alpha diketone moiety, an anthraquinone moiety, a thioxanthone moiety or benzoin moiety,
    and being present in an amount of 0.5 to 3 wt. % with respect to the weight of the dental adhesive composition.

5. The one-part dental adhesive composition according to claim 1, the stabilizer comprising a free radical moiety selected from 2,2-diphenyl-1-picrylhydrazyl, 4-hydroxy-2,2,6,6-tetramethyl-piperidine 1-oxyl, 2,2,6,6 tetramethyl-piperidinyloxyl, 2,6-di-tert-butyl-a-(3,5-di-tert-butyl-4-oxo-2,5-cyclohexadien-1-ylidene)-p-tolyloxyl, and triphenylmethyl radical.

6. The one-part dental adhesive composition according to claim 1, comprising in addition the following components alone or in combination:
    reducing agent(s) as Component B2;
    solvent(s) other than water as Component D1;
    filler(s) as Component F;
    polymerizable component(s) without an acidic moiety as Component G;
    functionalized organosilane(s) as Component H;
    additive(s) as Component I.

7. The one-part dental adhesive composition according to claim 1, comprising in addition the following components alone or in combination:
    reducing agent(s) as Component B2 in an amount of 0.1 to 2 wt. %;
    solvent(s) other than water as Component D1 in an amount of 5 to 40 wt. %,
    water as Component D2 in an amount of 1 to 20 wt. %;
    filler(s) as Component F in an amount of 0.5 to 10 wt. %;
    polymerizable component(s) without an acidic moiety as Component G in an amount of 5 to 60 wt. %;
    functionalized organosilane(s) as Component H in an amount of 1 to 10 wt. %;

additive(s) as Component I in an amount of 0 to 5 wt. %;
wt. % with respect to the weight of the dental adhesive composition.

8. The dental adhesive composition according to claim 1, comprising:
polymerizable component(s) with an acidic moiety in an amount of 3 to 20 wt. %,
photo-initiator(s) comprising an alpha-alpha diketone moiety in an amount of 0.5 to 3 wt. %,
transition metal ion component(s) selected from components comprising copper, iron or vanadium ions, in an amount of 0.01 to 1 wt. %,
solvent other than water in an amount of 5 to 40 wt. %,
water in an amount of 5 to 20 wt. %,
stabilizer(s) comprising a free radical moiety in an amount of 0.01 to 0.5 wt. %,
reducing agent(s) in an amount of 0.1 to 3 wt. %,
filler(s) comprising silica in an amount of 0.5 to 10 wt. %,
polymerizable component(s) without an acidic moiety in an amount of 5 to 60 wt. %,
functionalized silane comprising a (meth)acrylate moiety in an amount of 1 to 10 wt. %,
functionalized silane comprising an amino moiety in an amount of 1 to 10 wt. %,
additive(s) in an amount of 0 to 5 wt. %,
wt. % with respect to the weight of the dental adhesive composition.

9. The one-part dental adhesive composition according to claim 1, not comprising the following components alone or in combination:
organic boron containing component(s) in an amount of more than 0.2 wt. %;
sulfinic acid component(s) in an amount of more than 0.2 wt. %;
persulfate component(s) in an amount of more than 0.2 wt. %;
thiourea component(s) in an amount of more than 0.2 wt. %;
cysteine component(s) in an amount of more than 0.2 wt. %,
wt. % with respect to the weight of the dental adhesive composition.

10. The one-part dental adhesive composition according to claim 1, being a self-etching, self-adhesive dental composition.

11. The one-part dental adhesive composition of claim 10, being characterized by the following features alone or in combination:
viscosity: 0.01 to 3 Pats at 23° C. and a shear rate of 100 s-1;
pH-value: 0.8 to 4;
shear bond strength to dentin: at least 9 MPa;
being storage stable.

12. A kit of parts comprising:
a one-part dental adhesive composition of claim 1, and
a dental composite material comprising:
polymerizable component(s) without an acidic moiety,
filler(s), and
a redox-initiator system comprising an oxidizing agent and a reducing agent.

13. The kit of parts according to claim 12, the dental composite material being provided as a kit of parts comprising a base part and a catalyst part, wherein the oxidizing agent and the reducing agent are contained in different parts during storage.

14. The kit of parts according to claim 12, the dental composite material comprising in addition a photo-initiator system.

15. The kit of parts according to claim 12, comprising in addition the following parts alone or in combination:
dental filling composite;
dental sealant;
dental cement;
dental core build-up material;
dental milling blank;
hydrofluoric acid etchant;
instruction for use.

16. The one-part dental adhesive composition of claim 1, the transition metal component(s) selected from components comprising vanadium, chromium, manganese, iron, cobalt, nickel, copper, and a combination thereof.

17. The one-part dental adhesive composition of claim 1, the transition metal component(s) selected from copper acetate and vanadyl acetylacetonate.

18. The one-part dental adhesive composition of claim 1,
the stabilizer having a free-radical moiety selected from 2,2-diphenyl-1-picrylhydrazyl and 2,2,6,6 tetramethyl-piperidinyloxyl; and
the transition metal component(s) selected from copper acetate and vanadyl acetylacetonate.

\* \* \* \* \*